United States Patent
Ladjevardi

(10) Patent No.: US 7,489,816 B2
(45) Date of Patent: *Feb. 10, 2009

(54) ADVANCED COSMETIC COLOR ANALYSIS SYSTEM AND METHODS THEREFOR

(75) Inventor: Mahmoud Ladjevardi, La Jolla, CA (US)

(73) Assignee: Aevora Beauty Concepts, Inc., La Jolla, CA (US)

(*) Notice: Subject to any disclaimer, the term of this patent is extended or adjusted under 35 U.S.C. 154(b) by 23 days.

This patent is subject to a terminal disclaimer.

(21) Appl. No.: 11/561,280

(22) Filed: Nov. 17, 2006

(65) Prior Publication Data

US 2007/0100555 A1  May 3, 2007

Related U.S. Application Data

(62) Division of application No. 10/471,898, filed as application No. PCT/US02/24421 on Jul. 31, 2002, now Pat. No. 7,151,851.

(60) Provisional application No. 60/309,510, filed on Jul. 31, 2001, provisional application No. 60/311,448, filed on Aug. 9, 2001, provisional application No. 60/322,512, filed on Sep. 12, 2001.

(51) Int. Cl.
*G06K 9/00* (2006.01)

(52) U.S. Cl. .................................................... 382/167

(58) Field of Classification Search ................. 382/100, 382/162–167; 356/402–405, 421–423; 132/202–203; 8/400–405, 441

See application file for complete search history.

(56) References Cited

U.S. PATENT DOCUMENTS 5,643,341 A * 7/1997 Hirsch et al. .................... 8/405
6,067,504 A    5/2000 MacFarlane et al.
6,807,297 B1 * 10/2004 Tankovich et al. .......... 382/162

\* cited by examiner

*Primary Examiner*—Sherali Ishrat
(74) *Attorney, Agent, or Firm*—Fish & Associates, PC

(57) ABSTRACT

An advanced cosmetic color analysis system analyzes the color of a three dimensional object to produce a plurality of color values for distinct subsets of a portion of the object, and a cosmetic analyzer combines the color values to produce a cosmetic color determination that has relative weightings of multiple cosmetic colors. Contemplated systems are particularly useful for determination of suitable cosmetic products (or composition thereof) to achieve a particular and desired cosmetic appearance.

11 Claims, 1 Drawing Sheet

ADVANCED COSMETIC COLOR ANALYSIS SYSTEM AND METHODS THEREFOR

This application is a divisional application of allowed application with Ser. No. 10/471,898 filed Feb. 9, 2004, now U.S. Pat. No. 7,151,851 which is national stage entry of PCT/US02/24421, filed Jul. 31, 2002, which claims priority from provisional application 60/309,510, filed Jul. 31, 2001, provisional application 60/311,448, filed Aug. 9, 2001, and provisional application 60/322,512, filed Sep. 12, 2001.

FIELD OF THE INVENTION

The field of the invention is cosmetic color analysis, and especially hair color analysis.

BACKGROUND OF THE INVENTION

There are numerous systems and methods known in the art to determine color of an object, and depending on the particular application or type of object, color determination methods and systems may vary substantially. For example, many medical and other scientific applications prefer hyperspectral imaging, especially where precise measurement is necessary. Hyperspectral imaging typically provides spectral analysis (often with a resolution of less than 10 nm) of each pixel in a field, thereby generating excellent data on the object. For example, based on such imaging, tissue demarcations (such as may be present in neoplastic or other pathological conditions) may be readily identified.

In contrast, all or almost all known cosmetic applications exhibit a significantly less sophisticated degree of analysis. For example, MacFarlane et al. describe in U.S. Pat. No. 6,067,504 an analytic system in which color is averaged over an entire field, rather than on a pixel-by-pixel basis. Consequently, a major drawback of such systems is that the processes of averaging frequently provide false readings where one or more hair is present having different colors. For example, one person having some dark brown hair and some white hair would be found to have the same hair color as another person having all light brown hair. Yet the cosmetic effect of the two would be entirely different. Moreover, the two persons would likely need different hair color products to achieve the same end coloration.

More recent patent applications, WO 01/55956 and U.S. Pat. No. 09/493,511 (filed Nov. 3, 2000 and Jan. 28, 2000, respectively, and both incorporated by reference herein) describe analysis of subsets of a field during cosmetic color analysis of hair or skin. Such systems advantageously permit substantially increased accuracy of 'real-life' color using an ordinary video or other digital camera, as opposed to an expensive calorimeter. For example, the subsets can be analyzed down to a pixel-by-pixel level, which typically allows the system to compensate for shading, glare, and other effects.

However, despite improved color analysis, such systems still provide output as a single color reading. Therefore, blotchy skin or highlighted areas in an otherwise homogenous hair population will nevertheless be presented as a single color output. For example, on a descriptive scale the computed color may be presented as "light blonde", "auburn", or "silver". Alternatively, on a numeric scale the color may be presented as 1.78, 4.22, or 7.29.

Thus, although there are various methods and systems known in the art to determine the color of an object, and particularly of a cosmetic object, all or almost all of them suffer from one or more disadvantages. Therefore there is still a need to provide improved methods and systems for cosmetic color determination.

SUMMARY OF THE INVENTION

The present invention is directed to methods and systems in which a collector captures light reflecting off of a three dimensional object as a field of pixels, and in which a color analyzer uses data from the pixels to produce a plurality of color values for each of various distinct subsets (comprising more than one pixel) of the field. A cosmetic analyzer combines the color values from the various subsets and produces a cosmetic color determination that includes relative weightings of a plurality of cosmetic colors.

In one aspect of the inventive subject matter, the collector includes a digital video camera or a digital still camera. Therefore, it is generally preferred that the data from the pixels are RGB or CMYK encoded data (which may further include a hue, saturation, and/or luminance value). It is further preferred that the three dimensional object is a single hair, a plurality of hair, and/or a portion of facial skin.

In another aspect of the inventive subject matter, the color analyzer calculates the color values as a frequency of predetermined color combinations, and it is contemplated that, among other choices, the plurality of distinct subsets of the field is at least ten distinct subsets that may or may not be defined by a user, wherein the pixels in the plurality of distinct subsets of the field are preferably contiguous. The cosmetic color determination preferably comprises relative weightings of between and including two and four cosmetic colors, wherein the cosmetic color is expressed in a descriptive cosmetic term or in one or more numeric values.

In particularly preferred aspect of the inventive subject matter, the three dimensional object comprises hair and the cosmetic color determination includes an identification of a commercially available hair coloring product to achieve a predetermined coloration, or includes prediction of a hair color resulting from use of a commercially available hair coloring product. Alternatively, the cosmetic color determination may include calculation of a composition of a hair coloring product to achieve a predetermined coloration (typically comprising at least one color and at least one undertone). Where the three dimensional object comprises a single hair or a strand of hair, and where the cosmetic color determination comprises determination of a hair color distribution or determination of hair condition in the single hair or strand of hair, it is contemplated that the collector may be optically coupled to a magnifying device.

In yet further contemplated aspects, the three dimensional object is hair and the cosmetic color determination comprises recommendation of a commercially available customer specific hair care product to achieve a desired outcome, wherein particularly preferred hair care products are conditioners or shampoos (which may even be commercially available from a supplier other than a supplier that provides the system). It is still further contemplated that a storage medium may be electronically coupled to the cosmetic analyzer, wherein the storage medium stores usage history, results history, and/or personal data of a user, all of which may be used to further personalize and recommend choice of suitable products.

Various objects, features, aspects and advantages of the present invention will become more apparent from the following detailed description of preferred embodiments of the invention, along with the accompanying drawing.

DETAILED DESCRIPTION

Figure 1:
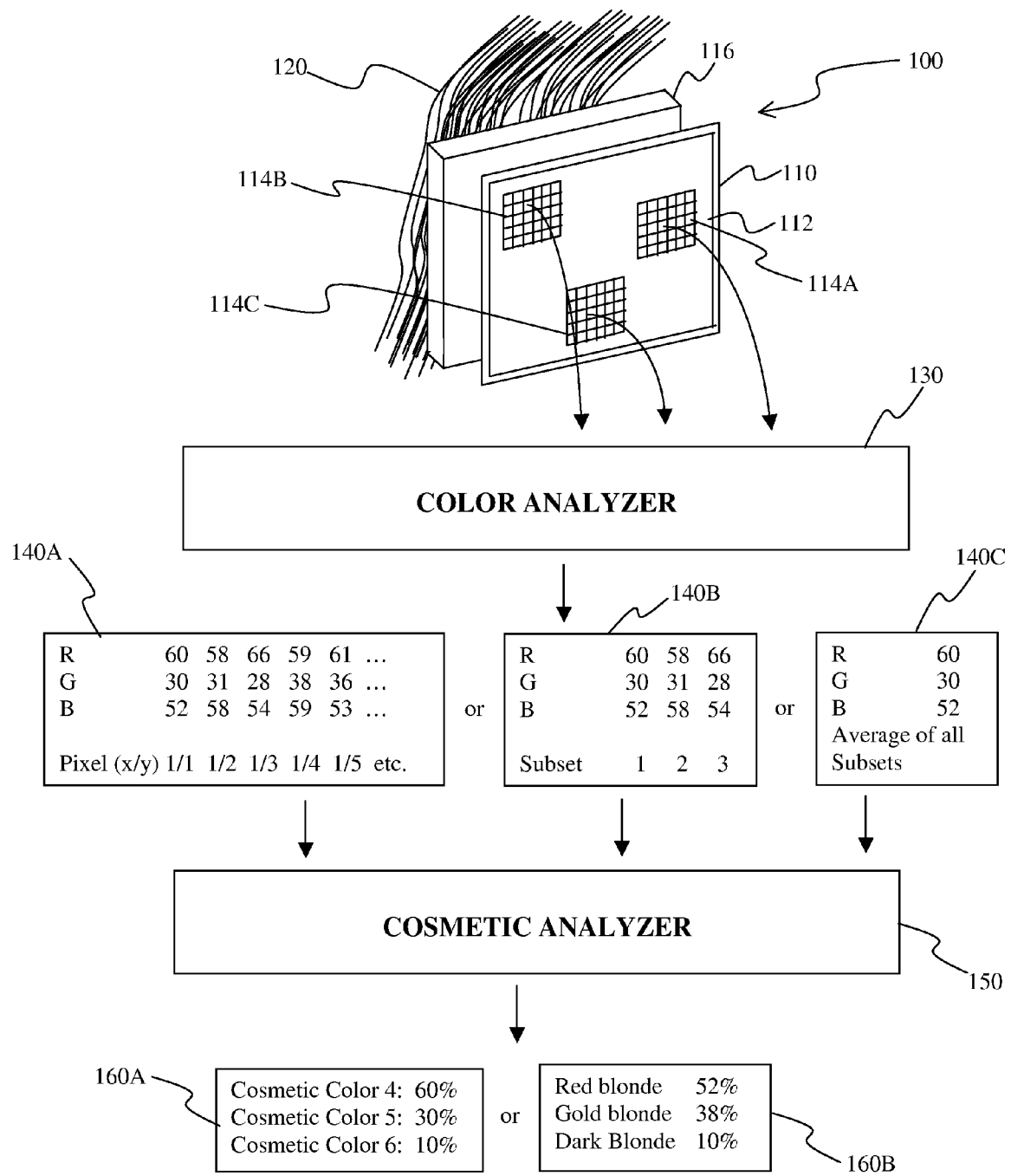
FIG. 1 is an exemplary schematic view of a cosmetic color determination system according to the inventive subject matter.

The inventor has discovered that significantly improved accuracy and representation of cosmetic color can be produced when computed color is presented as a plurality of color readings. In a particularly preferred aspect, cosmetic color is determined using a modified system (which may be marketed under the brand name, COLORMATCH™) similar to that described in U.S. Ser. No. 09/493,511 and PCT/US00/41879 applications, both incorporated by reference herein.

Therefore, it is generally preferred that contemplated systems include a collector that captures light as a field of pixels reflecting off of a three dimensional object, a color analyzer that uses data from the pixels to produce a plurality of color values for each of a plurality of distinct subsets of the field, wherein each distinct subset comprises more than one pixel, and a cosmetic analyzer that combines the plurality of color values from the subsets to produce a cosmetic color determination comprising relative weightings of a plurality of cosmetic colors.

An exemplary system 100 is schematically depicted in FIG. 1, in which a collector 110 has a field of pixels 112. An optical support system (e.g., magnifying device) 116 may be optically coupled to the collector, and the collector captures light reflecting off of a plurality of hair 120. Three distinct subsets 114A, 114B, and 114C of the field of pixels are analyzed in the color analyzer 130 that uses the data from the pixels to produce a plurality of color values for each of the distinct subsets of the field. Depending on the particular configuration (see below), the format of the plurality of color values may vary substantially, and FIG. 1 depicts only an exemplary representation of plurality of color values. Here, in one option 140A, the color of each individual pixel in each of the subsets is analyzed using an RGB system. In an alternative option as depicted as 140B, the color of each subsets is analyzed using an RGB system (e.g., by averaging the color of all of the pixels in a particular subset). In a further option, 140C, the average color of at least some subsets is analyzed using an RGB system (e.g., by averaging the color of all of selected subsets).

A cosmetic analyzer 150 then calculates cosmetic color (e.g., based on empirical algorithms or on user defined reference values) from the color values of the subsets to produce a cosmetic color determination comprising relative weightings of a plurality of cosmetic colors. One option of providing such cosmetic color determination is depicted in 160A in which the cosmetic color determination is output as a numeric values of known cosmetic compositions. Alternatively, as shown in 160B, cosmetic color determination may be output as numeric values of cosmetic terms.

In especially contemplated aspects, the collector is optically coupled to a digital video camera or a digital still camera, and may further include a light source that emits broad band light. However, it should be recognized that in alternative systems the collector need not necessarily be coupled to a camera, and suitable devices may include a CCD (charge coupled device) or other optical chip that receives the light reflected off the three-dimensional object. Similarly, it should be recognized that while a light source is preferably included, the type and number of suitable light sources may vary considerably. For example, where sufficient ambient light is available, a light source may be omitted altogether. On the other hand, and especially where the light quality (e.g., spectral composition and/or intensity) varies significantly, one or more incandescent or luminescent light sources may be coupled to the collector.

Still further, suitable systems may further include one or more filters to enhance capture of particularly desirable colors or to block colors that are not intended for further analysis. Alternatively, or additionally, contemplated systems may further comprise a window coupled to the collector, wherein the window may be removable, and/or include a color calibration region and/or a product identification region. For example, one function of the disposable window may be to improve the accuracy of the collector, color analyzer, and/or some other device by providing a color calibration region that can be used for calibration (While calibration may be realizable for any component, calibration is typically performed for the image collector or the color analyzer). Thus, it should be recognized that capture of the light reflecting off of the three dimensional object need not be limited to a particular spectral range, and it is contemplated that capture may be performed at one or more individual wavelengths (e.g., with bandwidth of between 1 nm to 20 nm, and more), one or more bands of wavelengths (e.g., UV range [e.g., between 240 nm-360 nm], VIS range [e.g., between 360 nm-740 nm], and/or IR range [e.g., between 740 nm-1040 nm]), and any reasonable combination thereof.

The process of calibration preferably comprises the image collector capturing at least one standardized sample of color from the calibration region in the window. From the sample of color, the image collector calculates a resultant measurement. The image collector may then be calibrated based on a calculation that includes a comparison between the resultant measurement and a predetermined measurement. Calibration of the image collector or other device preferably occurs before every capture of the three dimensional object. Alternatively, the disposable window may also be employed to encourage hygiene. Often the window will come in contact with a person's face or hair, and the possibility exists that the window may become dirty or otherwise contaminated. Simple cleaning of the window may be insufficient to remove the dirt or contamination.

Depending on the particular collector and hard- and software processing the data from the collector, it is contemplated that the data from the pixels may be encoded in various formats, and all known data formats are contemplated suitable for use herein. However, in particularly preferred aspects, the data are encoded in an RGB (red-green-blue) system or a CMYK (cyan-magenta-yellow-black) system. Furthermore, it is preferred that the data further comprise at least one of a hue value, a saturation value, and a luminance value.

In further contemplated aspects of the inventive subject matter, it is generally preferred that the color analyzer and the cosmetic analyzer are any electronic device capable of performing programmed instructions. Thus, particularly preferred electronic devices include a computer (e.g., desktop, laptop, internal microprocessor chip, etc.) having a color analyzer (e.g., image analysis software) and the cosmetic analyzer (e.g., database program comparing previously stored reference data with data provided from image analysis software).

Consequently, in one aspect of the inventive subject matter, the plurality of color values may be calculated on a pixel-bypixel basis for each distinct subset, especially where high resolution and/or information content is desired. Alternatively, it should be recognized that the plurality of color values may be calculated on a subset-by-subset basis, wherein the color values of the pixels in the subset may first be statistically analyzed (e.g., frequency distribution, average distribution, median distribution, etc.) before the color value for the subset is determined. Such color value determination is particularly useful where the object has relatively homogeneous color distribution. In a yet further aspect, the color value may be determined on a statistical analysis of more than one subset.

The term "distinct subset" as used herein refers to a plurality of pixels (i.e., more than one and less than the total number of pixels) in the field of pixels, wherein the pixels may be randomly distributed or contiguous. Similarly, it should be recognized that a plurality of distinct subsets may be in a predetermined or random location on the field of pixels. Furthermore, it should also be recognized that the plurality of pixels and/or the distinct subsets of pixels may be user defined (e.g., via screen output and mouse control). In preferred aspects, the plurality of distinct subsets of the field is at least ten, and more typically at least hundred distinct subsets.

Therefore, it should be recognized that the particular format of contemplated color values may vary substantially. For example, where the color value is determined on a pixel-by-pixel basis, the color output may be in 256-bit color format, high color format (16 bit), or true color format (32 bit). Thus, each distinct subset may provide multiple color values (corresponding to the number of pixels). Alternatively, where desired, the color values of the pixels in each distinct subset may be statistically analyzed (e.g., frequency distribution, average distribution, median distribution, etc.) to provide a color value for the particular distinct subset. In still other aspects, the color value for the distinct subset may also be determined as a frequency of predetermined color combinations, wherein the predetermined color combination may be made on the basis of economical consideration (e.g., no more than ten variations per commercially available hair tone) or scientific considerations (e.g., capability of the human eye to determine distinct colors). Still further encoding manners may be found in "Digital Color Management: Encoding Solutions" by Edward J. Giorgianni and Thomas E. Madden (Prentice Hall PTR; ISBN: 0201634260).

With respect to the cosmetic color determination it is generally contemplated that the determination will be made at least in part on a comparison of the color values with a set of reference colors. In a typical cosmetic color determination, the color values may be combined from a plurality of pixels and/or distinct subsets to form an average color value, or to form a histogram of color distribution over the selected pixels and/or distinct subsets. Alternatively, the color values may be individually compared on a pixel-by-pixel or subset-by-subset basis. The reference colors in contemplated systems may preferably be obtained by measuring the color of known samples (e.g., for hair dying product hair samples dyed with a particular color). Alternatively, reference colors may also be calculated using a theoretical hair model. Comparison of the color values and the reference color may be performed using numerous models, and it is contemplated that all known color comparison methods are contemplated suitable for use herein (see e.g., "Color Theory and Modeling for Computer Graphics, Visualization, and Multimedia Applications" by Haim Levkowitz, Kluwer Academic Publishers; ISBN: 0792399285).

Regardless the manner of obtaining and comparing the color value with the reference color, it is contemplated that the cosmetic analyzer uses (e.g., combines) the plurality of color values from the distinct subsets to produce a cosmetic color determination that has relative weightings of a plurality of cosmetic colors. The term "cosmetic color" as used herein refers to an apparent color, used in a cosmetic sense, rather than an actual scientific color expressed merely as a reflectance at one wavelength or another. For example, the term "dark blonde" is considered a cosmetic color of a dark blonde hair. Alternatively, a reference to a (standard) hair color nomenclature may be considered as a cosmetic color (e.g., Natural 4), or an absolute numeric value that has a correspondence to a known hair color (e.g., 1.6 corresponding to medium brown). In contrast, a listing of spectral absorbance of a dark blond hair between 360 nm and 740 nm at a 5 nm resolution is not considered a cosmetic color under the scope of this definition.

In particularly preferred aspects, the determination has relative weightings of at least two, and more preferably between two and four (inclusive) cosmetic colors, wherein the cosmetic color is most preferably expressed in a descriptive cosmetic term. For example, a suitable cosmetic color determination may provide as output for a particular hair color as "21% Natural 3, 66% Natural 4, and 13% Natural 5", or "78% medium brown and 22% dark brown". Similarly, where a visual calibration scale is available, numeric values may be provided and the output may then read as "21% of 1.6, 66% of 1.8, and 13% of 2.2".

Furthermore, the nature of the three dimensional object need not be limited to a particular object so long as the object is substantially three dimensional. The term "substantially three dimensional" as used herein refers to any object having a length, width, and depth. For example, a single hair, or strand of hair is considered a three dimensional object because a single hair or strand of hair has a particular length, width, and depth. In contrast, a photographic image (e.g., Polaroid picture) of a single hair or strand of hair is not considered a three dimensional object since the hair or strand of hair in the photographic image lacks depth. Consequently, particularly suitable three dimensional objects include animate objects, and/or objects grown or otherwise attached to animate objects, and are most preferably selected from the group consisting of a hair, a plurality of hair, and a portion of facial skin. Depending on the particular size of the three dimensional object (or on the desired degree of detail), it is especially contemplated that the collector in contemplated devices may be optically coupled to a magnifying device (e.g., microscope, zoom lens, etc.).

In particularly preferred aspects of the inventive subject matter, the three dimensional object comprises hair and the cosmetic color determination further comprises identification of a commercially available hair coloring product to achieve a predetermined coloration, or the three dimensional object comprises hair and the cosmetic color determination further includes prediction of a hair color resulting from use of a commercially available hair coloring product. In yet further preferred aspects, the three dimensional object comprises hair and the cosmetic color determination further comprises calculation of a composition of a hair coloring product to achieve a predetermined coloration. Such calculation may be especially advantageous where the composition of the hair coloring product includes at least one color and an undertone to assist a user in finding a suitable composition for a desired result.

In still further preferred aspects, the three dimensional object comprises a single hair or a strand of hair, and the cosmetic color determination further comprises determination of a hair color distribution in the single hair or strand of hair. Where only a few, or even a single hair is measured using contemplated systems, it should be recognized that the cosmetic analyzer may combine the plurality of color values from the subsets to produce a hair condition determination. For example, a typical hair condition determination may include determination of waviness, curliness, thickness, texture, condition, and/or integrity of at least one hair. Consequently, it is contemplated that the cosmetic color determination may also encompass recommendation of a commercially available customer-specific hair care product (e.g., conditioner or a shampoo, which may even be commercially available from a supplier other than the supplier that provides the system) to achieve a desired outcome.

In yet another preferred aspect, contemplated cosmetic analyzers may further include a storage medium that is electronically coupled to the cosmetic analyzer, wherein the storage medium stores various parameters associated with a user and or a cosmetic product. For example, it is contemplated that user data may include usage history and/or results history, while product information may include availability, cross references to a competitor's product, etc.

In one exemplary use, the field is preferably captured using a color video camera, and then analyzed according to pixel subsets, and possibly even on a pixel-by-pixel basis. Software then determines which pixels relate to the same hair, what the color is of each hair, and the relative amounts of each hair. Alternatively, color could be determined for each pixel or other subset, and then the amounts of each color are added together to provide a final result.

For example, as opposed to its COLORMATCH™ predecessor, the currently contemplated hair color analyzer will provide a plurality of responses corresponding to individual hair colors in which the magnitude of individual responses will depend on relative representation of standard (signature) colors in the image, and wherein the standard colors can be defined in advance based on color swatch book provided by hair color manufacturers (e.g. Aveda™ Full Spectrum book. The signature colors can be measured using COLORMATCH™ calibration package and stored in a COLORMATCH™ database), or any other suitable means.

Once the camera captures a hair image, the hair color analyzer can scan individual pixels and compare the camera readings against signature data contained in the database. For each pixel a closest match will provide a unit response in the hair color spectrum. Upon completion of the image scan, the spectrum will represent a cumulative picture of how often various signature colors have been encountered in the captured image. For example, if only Natural 6 color is present in the image all unit responses will be accumulated in a corresponding bin of the hair color spectrum and it will have a single peak at this particular color. On the other hand should Natural 5, 6 and 7 colors be present in certain proportion the unit responses would be accumulated in corresponding bins and three nonzero peaks in the spectrum will be observed.

After the hair color spectrum is constructed, a decision will be made using a maximum likelihood principle or other statistical method on whether (a) a single color dominates all the others, (b) several similar colors are present simultaneously and in comparable proportions (e.g. 40% of Natural 7 and 50% of Ash 7), and/or (c) several dissimilar colors are present (e.g. 60% of Natural 4 and 25% of Natural 8). This case is likely to occur if the hair color is highly inhomogeneous due to highlights or gray hair. In addition to the above capabilities the hair color analyzer may also incorporate interference reduction algorithms similar to those used in the COLORMATCH™ package. The purpose of those algorithms is to recognize and to remove from the image pixels having color non-characteristic for the hair (e.g. skin color) so that only the hair color is analyzed.

In yet another exemplary use of contemplated systems, a customer uses the contemplated system to determine his or her starting hair color and undertone. From the available hair colors choices represented by box pictures and/or hair swatches on the retail store shelf, the customer selects and then inputs his or her desired hair color and undertone result into the system. The contemplated system will then not only recommend the correct box of hair color to purchase, but will also prescribe the type and quantity of undertone that the customer must mix into the purchased color formula based on previously stored reference data.

One especially attractive embodiment of such coloring systems, would include a container that dispenses undertone dyes by turning a dial. Each times the dial clicks, one dose of undertone has been dispensed, and the container has been resealed again to guard against oxidation of remaining undertone. This will ensure that the correct quantity has been added and will guard against mistakes. Another embodiments might include a simple dropper to dispense the undertone dye.

Thus, contemplated systems will determine a person's starting hair color(s) in an early step in the hair coloring process. Armed with this data, and coupled with the knowledge of the specific hair color and undertone that the person desires, a customized color formulation can be prepared to change the person's specific starting hair color to the desired color and shade. In contrast, currently, manufacturers of "at-home" hair color kits that are sold in retail stores offer limited assortment of up to 40 color and undertones (shade) choices. This limited and static choice of colors means that most users will not be able to achieve the hair colors that are shown in the pictures that adorn the hair color boxes, the pictures on the hair color boxes do not guarantee actual results, since typically only people with specific starting hair color and undertone can achieve the results shown on the boxes.

For example, someone with a predominance of red undertones in their hair cannot achieve the natural blonde result that a box of #9 hair color may showcase. If this user applied the Natural #9 level hair color, his or her red undertones will produce blonde hair with reddish tint. To match the desired box color, one must add Ash undertone to the Natural #9 hair color to counteract the existing reddish undertone, which is typically only done in professional hair salons and has generally not been available to retail customers of "at-home" hair color, primarily because it has been extremely difficult for a non-professional to estimate the type and quantity of undertone that users require for their individual starting hair color, and in relation to their desired hair color and shade.

It is further contemplated that suitable systems will readily incorporate a relational database of hair color formulations to its existing hair color determination system to spell out the correct formulations for various hair color and undertone starting points, and different desired hair colors and shades. Among other things, such a database may register the specific formulations for each of the existing 30-40 SKU of hair color that are being sold in retail stores, and coordinate that information with possible starting hair colors and shades. Formulas can be used to predict which of the retail products should be used with which amounts of undertone in each instance A significant advantage is that all of this can be done without expanding the existing number of products on the shelf.

Consequently, a manufacturer using contemplated systems should have a significant competitive advantage in the market place. Not only does the system guard against most user mistakes, but it can also provide results that are likely close to those of professional hair salons having well trained and experienced colorists. Moreover, it is expected that this system (a) will stimulate trial, usage and experimentation among existing and new users, among other things because it makes the use of undertone additives easy, safe, and reliable; (b) will draw and convert competitor's customers; and/or (c) will draw and convert some professional hair salon customers or encourage salon customers to use contemplated systems as an interim solution in between visits. When employed in a professional setting, contemplated systems will provide greater predictability and reproducibility. It also empowers junior and experienced colorists to work more confidently and faster.

Still another advantage is that a manufacturer need not make any costly changes to its currently marketed product line. It will thus save the cost of replacing, transitioning and re-launching product. The manufacturer simply adds a few undertone SKUs to its product line, and in the process exponentially increases the possible range of color formulations and results.

It should be especially recognized that numerous benefits arise from the use of contemplated systems. For example, in addition to analyzing the color of the hair as a whole, multiple subset analysis can be used to determine color of individual strands or even portions of strands. Among other things, such information may be useful in limiting or expanding a list of realistic color choices. A particularly useful variant may be to electronically identify a portion of hair that is close to the scalp, and then determine how the coloration of that portion differs from other portions of the hair. In that manner one could identify the "natural color" of a person's hair and determine if user's hair has been previously colored; regrowth of natural hair color appears at the root and close to the scalp and if its color(s) differs from the rest of the hair, it can be surmised that user's hair had previously been colored. Subsequently, comparing and contrasting the colors at the root with the rest of the hair will determine the best course of action for recoloring hair. For example, if the hair was previously colored blonde and the regrowth at the root is black, the system will determine that to color the regrowth blonde, requires double-processing and simply applying blonde color will produce poor results. This will prevent incorrect product use and customer mistakes.

Moreover, by analyzing individual strands, one can also obtain a percentage of gray hair versus non-gray hair. Since gray hair may react differently from non-gray hair to various colorants, knowing the percentage of gray hair can be useful in choosing among colorants, processes, and so forth. Such information can also be important in making a threshold choice among colorants as a function of whether one is trying to change the hair color, or merely trying to "cover" the gray hair. Yet another possibility is that the knowledge of the amount of gray hair may help determine a subset of hair colorants that are appropriate or inappropriate for an individual user.

In another example, multiple subset analysis can be used to determinate to condition of hair, including texture, thickness, waviness, curliness, and so forth, which can be achieved by electronically identifying portions of individual strands, and then estimating the directionality and thickness of such strands. Furthermore, through electronic or optical magnification, the condition of individual strands of hair can be determined. For example, it is possible to identify split ends and strand breakage. The outer sheath of the hair can also be examined to develop information about the sheen, texture, and other characteristics of the hair.

In a further example, it is contemplated to use data secured through multiple subset analysis to recommend hair care products, including for example shampoos and conditioners. Among contemplated scenarios, a system may determine that a customer's hair has been colored with red undertones, and may therefore recommend a shampoo that enhances and maintains the red undertones in the hair. In another possibility, a system may determine that a customer's hair requires a high degree of chemical processing to deliver the desired result and may therefore recommend a special conditioner to hydrate and condition the hair. In yet another possibility, a system may determine that a customer's hair has microscopic damage to individual strands, and may therefore recommend a polymer containing conditioner. Depending on the sheen of the hair, a system may recommend a shampoo having greater or lesser oil content.

In yet another example, contemplated systems may be adapted to the experience and particular product line(s) of a given vendor. For example, a vendor would choose to have the system make recommendations with respect to its own colorants, hair care, and other products. However, under certain circumstances contemplated systems may also make recommendations with respect to products of a competing vendor. Thus, a system funded by CLAIROL™ could make recommendations to both CLAIROL™ and L'OREAL™ products. More likely, however, a system funded by a given vendor would query a user about a previously used or contemplated competitor's product, and then make a recommendation to use an equivalent product from its own product line.

It is also contemplated that a company may want to avoid the cost of installing and maintaining systems such as those set forth herein, or may want to take advantage of a system installed by another for some other reason. In such cases one may advantageously provide a cross-reference product guide that would cross-sell a different product line from than recommended by the system. Thus, if a competitor wanted to take advantage of a previously installed hair color determination system, the competitor might provide a printed or electronic cross-reference chart that would recommend the competitor's products in place of the computer-recommended products.

In a still further example, and especially where contemplated systems are used to capture and store usage and results history for individual customers, it is contemplated that a customer may have uncolored hair with a color value of 5, and the system may recommend a particular product. That information can be stored in a database, and over time such information from numerous consumers can be used to track customer choices for marketing purposes. Furthermore, a customer may apply a product, and then return for a follow up analysis. The follow up can be performed in any suitable time frame, including shortly after applying the product, up to several months later, or both. The system could then develop a database regarding the effects of particular products on an individual's hair, and use that information in recommending specific products. For example, if a system knew that a particular person's hair took dark color very poorly, or perhaps was extremely resistant to bleaching, that information may be extremely useful in suggesting that a customer limit her choices of future products or procedures to a particular subset that avoids problematic choices.

Some or all of this information may be stored locally or distally with respect to the system. It may be advantageous, for example, to store the information on a national or cross-national database, and then provide customers with their personal information through the Internet or other network. Such information could be used to help educate a customer as to why particular results were obtained, with respect to cross-selling and new products, and so forth. Of particular interest is the possibility of individualized on-line accounts, where a customer can access her coloring history to learn specifically what products are suitable for her individualized needs and characteristics, learn about hair coloring in general, experiment with digital examples of possible new hair styles, colors, and so forth. Cross-selling of other products is also contemplated, especially but not necessarily with respect to beauty products.

Vendors can also make indirect use of historical hair coloring information in their marketing, and research and development efforts. For example, if a vendor learns through the database that very few people on a percentage basis change from hair color A to hair color B, then it might be wise to devote only very limited resources to that particular color change. In another possibility, if a vendor learns through the database that a very large subset of customers have not achieved satisfactory results when attempting to change from color C to color F, then it might be wise to reconsider its product line and target more resources to specific new products and formulations.

Similarly, contemplated systems may be adapted to include personal information that is useful in making product recommendations, marketing, and follow up. For example, a system may seek information regarding a customer's gender, ethnic background, age, skin tone, eye color, and so forth. That information can be very useful in making product recommendations because they affect the coloration properties of hair. Alternatively or additionally, such information can be used in recommending shampoos, conditioners, and so forth, as well as products other than hair care products.

Thus, specific embodiments and applications of improved cosmetic color determination systems have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A method of customizing a hair colorant for a customer, comprising:
   acquiring light reflecting off of a three dimensional object as a field of pixels;
   calculating a plurality of color values for each of a plurality of distinct subsets of the field using data from the pixels, wherein each distinct subset comprises more than one pixel; and
   combining the plurality of color values from the subsets to produce a cosmetic color determination comprising relative weightings of a plurality of cosmetic colors.

2. The method of claim 1 wherein acquiring the light is performed using at least one of a band of wavelengths between 240 nm-360 nm, a band of wavelengths between 360 nm-740, and a band of wavelengths between 740 nm-1040 nm.

3. The method of claim 1 wherein acquiring the light is performed at one or more individual wavelengths with bandwidth of between 1 nm to 20 nm, and with a wavelength of between 240 nm and 1040 nm.

4. The method of claim 1 wherein the data from the pixels are encoded in an RGB system or a CMYK system, and wherein the data further comprise at least one of a hue value, a saturation value, and a luminance value.

5. The method of claim 1 wherein the plurality of color values is calculated as a frequency of predetermined color combinations.

6. The method of claim 1 wherein the cosmetic color determination comprises relative weightings of between and including two and four cosmetic colors.

7. The method of claim 1 wherein the three dimensional object is selected from the group consisting of a hair, a plurality of hair, and a portion of facial skin.

8. The method of claim 1 wherein the three dimensional object comprises hair and wherein the cosmetic color determination further comprises identification of a commercially available hair coloring product to achieve a predetermined coloration.

9. The method of claim 1 wherein the three dimensional object comprises hair and wherein the cosmetic color determination further comprises prediction of a hair color resulting from use of a commercially available hair coloring product.

10. The method of claim 1 wherein the three dimensional object comprises hair and wherein the cosmetic color determination further comprises calculation of a composition of a hair coloring product to achieve a predetermined coloration.

11. The method of any one of claim 8, claim 9, or claim 10 wherein the composition of the hair coloring product includes at least one color and an undertone.

* * * * *